(12) United States Patent
Weitz

(10) Patent No.: US 7,288,760 B2
(45) Date of Patent: Oct. 30, 2007

(54) CONFORMATIONAL REAL-TIME ATMOSPHERIC AND ENVIRONMENTAL CHARACTERIZATION SAMPLING APPARATUS AND METHOD

(75) Inventor: Karl K. Weitz, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 337 days.

(21) Appl. No.: 11/165,082

(22) Filed: Jun. 22, 2005

(65) Prior Publication Data

US 2007/0023641 A1    Feb. 1, 2007

(51) Int. Cl.
B01D 59/44 (2006.01)
B01D 15/08 (2006.01)

(52) U.S. Cl. .............. 250/288; 73/23.37; 73/23.42

(58) Field of Classification Search ............ 250/288; 600/532, 509; 356/338, 340
See application file for complete search history.

(56) References Cited

U.S. PATENT DOCUMENTS

| | | | |
|---|---|---|---|
| 5,237,175 A | | 8/1993 | Wells |
| 5,610,835 A | * | 3/1997 | Dominguez et al. .......... 702/24 |
| 5,872,306 A | * | 2/1999 | Arnold .................... 73/23.37 |
| 7,029,921 B2 | * | 4/2006 | Lee et al. ................. 436/148 |
| 2005/0137491 A1 | * | 6/2005 | Paz et al. ................... 600/543 |
| 2006/0060004 A1 | * | 3/2006 | Desrochers et al. ....... 73/863.71 |

OTHER PUBLICATIONS

Karla D. Thrall, A Real-Time Method to Evaluate the Nasal Deposition and Clearance of Acetone in the Human Volunteer, Inhalation Toxicology, 15, 2003, pp. 523-538.
Poet, et al. PBPK Modeling of the Percutaneous Absorption of Perchloroethylene from a SoilMatrix in Rats and Humans, Toxicological Sciences 67, 17-31, 2002, pp. 17-31.
Gordon, et al., Volatile Organic Compounds as Breath Biomarkers for Active and Passive Smoking, Environmental Health Perspectives, vol. 111,#7, Jul. 2002, pp. 689-698.
Rick Cee, Carbon Dioxide in Workplace Atmosphers, Inorganic Method #172, Jun. 1990, pp. 1-13.
Majidi, et al. Explicit chemical speciation by microsecond pulsed glow discharge time-of-flight mass spectrometry, J. Anal At. Spectrom, 2000, 15, pp. 19-25.

* cited by examiner

*Primary Examiner*—Nikita Wells
*Assistant Examiner*—Johnnie L Smith, II
(74) *Attorney, Agent, or Firm*—James D. Matheson

(57) ABSTRACT

The present invention relates generally to a method and apparatus for real-time environmental gas sampling. A manifold is disclosed allowing for real-time gas sampling and monitoring/analysis of atomospheric over a wide range of oxygen contents, e.g., oxygen-rich as well as oxygen-deficient sampling environments in conjunction with mass-sepectrometric analysis achieving detection limits as low as single part per-billion.

35 Claims, 9 Drawing Sheets

CONFORMATIONAL REAL-TIME ATMOSPHERIC AND ENVIRONMENTAL CHARACTERIZATION SAMPLING APPARATUS AND METHOD

FIELD OF THE INVENTION

The present invention relates generally to a conformational real-time atmospheric and/or environmental sampling and characterization apparatus and method. More particularly, the invention relates to a fully conformational real-time atmospheric and/or environmental sampling and characterization apparatus and method for sampling, monitoring, and analyzing analytes present in a range of oxygen environments (i.e., from oxygen-rich to oxygen-deficient) in conjunction with mass-spectrometric analysis.

SUMMARY OF THE INVENTION

In one aspect, the invention is a method for sampling, monitoring, and/or analysis of an analyte(s) in an atmospheric sampling environment or volume in real time, comprising: providing a manifold comprising: a throughput valving means operable for coupling to an atmospheric or other sampling environment; an inlet valving means for introducing an atmospheric or other sample containing an analyte(s) of interest into a mass-selective detector, component, or instrument; a fractioning means operably coupled to: (i) a pumping means, (ii) the inlet valving means, and (iii) the throughput valving means for fractioning the sample; and, wherein the manifold is fully conformational with the sampling environment and the detector, component, or instrument whereby a selectable flow of the sample is introduced into the mass-selective detector, component, or instrument at the operational vacuum or pressure for the detector, component, or instrument by the inlet valving means, the coordinated operation of the throughput valving means and the inlet valving means permitting sampling, monitoring, and/or analysis of the analyte(s) in the sampling environment in real-time.

In an embodiment, the sampling environment or volume is an oxygen-rich sampling environment or volume.

In another embodiment, the sampling environment or volume is an oxygen-deficient sampling environment or volume.

In another aspect, the manifold comprises: adjustable throughput valving means operable for coupling to an atmospheric or gas sampling environment; adjustable inlet valving means for introducing an atmospheric, or other gas sample containing an analyte(s) of interest into a mass-selective detector, component, or instrument; a pumping means operably coupled to the inlet valving means and the throughput valving means; and, wherein the throughput valving means and the inlet valving means are operably coupled providing coordinated adjustment whereby the manifold is fully conformational with both the atmospheric or sampling environment and the detector, component, or instrument, whereby a selectable flow of the sample is introduced into the mass-selective detector, component, or instrument at the operational vacuum or pressure for the detector, component, or instrument by the inlet valving means, the coordinated operation of the throughput valving means and the inlet valving means permitting sampling, monitoring, and/or analysis of the analyte(s) in the sampling environment in real-time.

In an embodiment, the manifold is a component of a system or device for real-time monitoring/detection of toxic, environmentally hazardous, and/or industrially generated analytes in a sampling environment or volume.

In another embodiment, the manifold is configured for real-time measuring and monitoring of analytes released (respired) from an animal in an exposure study to chemicals absorbed through the skin of the animal.

In another embodiment, the manifold is configured for real-time measuring and monitoring of sampling environments having a head space, e.g., fermentation processes (e.g., breweries and wineries), fuel processes (e.g., of hydrogen produced in/from fuel cells).

In yet another embodiment, the manifold is configured for real-time measuring and monitoring of environmental gases indicating leaks in personal protection equipment and clothing.

In another embodiment, the manifold is a component of a real-time offgassing, exhausting, and/or emission monitoring or detection system.

In yet another embodiment, the manifold is configured for real-time measuring and monitoring of analytes in conjunction with environmental tolerances and limits testing, e.g., in offgassing, exhausting, and/or emission testing.

In yet another embodiment, the manifold is configured for real-time measuring and monitoring of analytes in air sampling environments in conjunction with, e.g., EPA environmental release limits and/or EPA environmental testing.

In yet another embodiment, the manifold is configured for real-time measuring and monitoring of metabolic processes, e.g., physical fitness (e.g., oxygen exchange efficiency), metabolic states (e.g., acetone and/or ketones as a measure of ketosis), disease states (e.g., cancer biomarkers), and the like.

In still yet another embodiment, the manifold is configured for real-time measurement of toxic, hazardous, and/or chemical/biological agents with, e.g., releases from processing plants (e.g., enrichment of nuclear fuels), terrorist actions (e.g., dispersion of agents), concealed materials transport (e.g., in luggage, cargo, etc.), airport security, and the like.

In another aspect, the invention is a manifold, comprising: a throughput valving means operable for coupling to an atmospheric sampling environment or volume; an inlet valving means for introducing an atmospheric or other sample containing an analyte(s) of interest into a mass-selective detector, component, or instrument; a fractioning means operably coupled to: (i) a pumping means, (ii) the inlet valving means, and (iii) the throughput valving means for fractioning a gas sample; and, wherein the manifold is fully conformational with the sampling environment and the detector, component, or instrument whereby a selectable flow of the sample is introduced into the mass-selective detector, component, or instrument at the operational vacuum or operational pressure for the detector, component, or instrument by the inlet valving means, the coordinated operation of the inlet valving means and the throughput valving means permitting sampling, monitoring, and/or analysis of the analyte(s) in the sampling environment in real-time.

DETAILED DESCRIPTION

Figure 1:
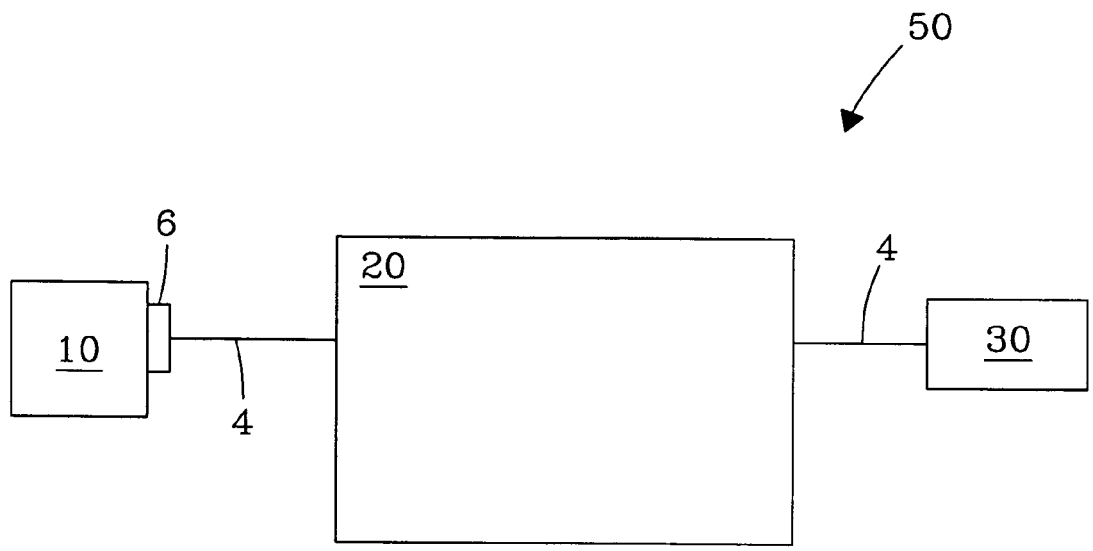
FIG. 1 illustrates a complete air sampling/analysis system incorporating a conformational atmospheric gas sampling manifold for real-time monitoring and analysis of sampling environments in conjunction with mass-selective detection, according to an embodiment of the invention.

While the present disclosure is exemplified by specific embodiments, it should be understood that the invention is not limited thereto, and variations in form and detail may be made without departing from the spirit and scope of the invention. All such modifications as will be envisioned by those of skill in the art are hereby incorporated.

The present invention generally relates to an apparatus and method for monitoring/analysis of analyte(s) from a wide variety of atmospheric and/or environmental gas sampling environments. More particularly, the invention relates to an apparatus and method for fully conformational real-time atmospheric and/or environmental sampling and characterization for sampling, monitoring, and analyzing analytes present in a range of oxygen environments (i.e., from oxygen-rich to oxygen-deficient) in conjunction with mass-spectrometric analysis in real-time.

The term "real-time" as used herein refers to sample analysis response times that are nearly instantaneous, providing analytical results for analyte(s) from sampling, monitoring, and/or analysis that are responsive to events in the sampling environment being monitored and/or analyzed. The term "conformational" as used herein refers to the apparatus and method of the invention being dynamically and fully adaptable to the sampling environment, e.g., to any selected throughput or flow rate from the sampling environment, and dynamically adjusting flow of a gas sample (e.g., at a variable and/or selectable flow rate) into a mass-selective detector, component, or instrument optimized to the operational pressure or vacuum of the detector, component, or instrument such that low detection limits and maximum peak intensities for the desired analyte(s) in the atmospheric or environmental sample are achieved. For example, as will be understood by those of skill in the art, flow rates and vacuum pressure requirements into a mass-selective detector, component, or instrument of system 10, as well as associated peak intensities of target analytes, can be optimized and/or maximized in conjunction with, e.g., an ion gauge (e.g., for vacuum monitoring) or other flow meter or gauge, including digital forms thereof. In a typical animal exposure study, for example, flow rates of individual manifold components may be dynamically adjusted to the respiration rate of the animal such that gas samples taken from the sampling environment contain analyte(s) truly representative of the environment being sampled, e.g., no dilution. In another example, e.g., in a sampling environment adapted for monitoring of head space volumes, e.g., fermentation processes, fuel cell processes, flow rates from the sampling environment are low. Due to the dynamic conformational nature of the apparatus and method of the invention, flow and throughput rates conform and/or adapt to the essentially static sampling environments. Peak intensities for analytes of interest are also further maximized in that flow rates into a mass-selective instrument, detector, or other component conform to the vacuum or operational pressure of the mass-selective detector, component, or instrument thereby achieving low analytical detection limits, e.g., as low as single parts-per-billion (ppb). No limitations are hereby intended. The term "oxygen-rich" as used herein refers to samples having an oxygen content of greater than or equal to about 20 percent by volume. The term "oxygen-deficient" as used herein refers to samples having an oxygen content of less than or equal to about 20 percent by volume.

FIG. 1 illustrates a system 50 for monitoring and/or analysis of samples from an atmospheric or other gas sampling environment 30 in real-time, according to an embodiment of the invention. System 50 comprises a fully conformational manifold 20 for transferring and metering atmospheric or other gas samples to an analysis system 10 comprising, e.g., a mass-selective (MS) detector, MS component, or MS instrument, providing for real-time monitoring and/or analysis of analyte(s) in sampling environment 30. Manifold 20 couples to the MS detector, component, or instrument system 10 via mounting means 6 (e.g., plate, bracket, or other connecting means) as will be known to those of skill in the art. No limitations are hereby intended. Components within system 50 link to manifold 20 via, e.g., ¼-inch I.D. stainless steel tubing, piping, or conduit 4, and associated fittings (e.g., Swagelok® fittings, available from Swagelok Co., Solon, Ohio), but are not limited thereto. Manifold 20 will now be further described in reference to FIG. 2.

Figure 2:
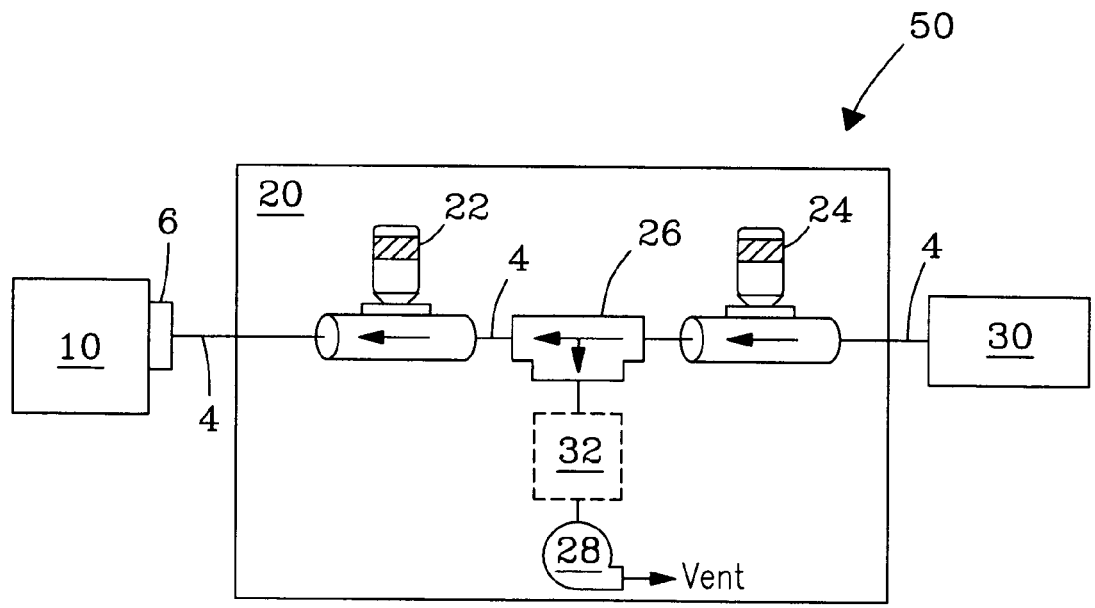
FIG. 2 illustrates a longitudinal view of a conformational atmospheric gas sampling manifold, according to an embodiment of the apparatus of the invention.

FIG. 2 presents a longitudinal view of a conformational atmospheric gas sampling manifold 20, according to an embodiment of the invention. Manifold 20 comprises inlet valving means 22, throughput valving means 24, fractioning means 26, and pumping means 28. Inlet valving means 22 include, but are not limited to, e.g., metering valves, vacuum valves, pressure valves, mass-flow controllers, digital versions thereof, electric or pneumatic versions thereof, or other valving means having a selectable flow rate for metering volatile and semi-volatile sample(s) into an analysis or monitoring system 10 comprising, e.g., a mass-selective (MS) detector, component, or instrument. Throughput valving means 24 include, but are not limited to, e.g.; metering valves, vacuum valves, pressure valves, mass-flow controllers, digital versions thereof, electric or pneumatic versions thereof, and/or other valving means having a selectable flow rate for coupling and conforming (e.g., adaptable to each sampling environment) to a atmospheric sampling environment 30 whereby atmospheric and other volatile and semi-volatile sample(s) introduced to manifold 20 from environment 30 are metered selectively into analysis system 10 for monitoring and/or analysis of analytes present in environment 30.

Mass-selective instruments include, but are not limited to, mass spectrometers, including MS/MS-type instruments, MS$''$ instruments, tandem mass spectrometers, quadrupole mass spectrometers, time-of-flight (ToF) mass spectrometers, FT-ICR mass spectrometers, ion-trap mass spectrometers, and/or other mass-selective components and devices. Sample fractioning means 26 include, but are not limited to, e.g., 3-way and 4-way unions, n-way connectors, T-connectors, n-way port valves, vacuum valves, and/or other fractioning means for i) fractioning sample(s), and ii) scrubbing particulates from sample(s) introduced to analysis/monitoring system 10, sample fractioning means 26 being disposed between throughput valving means 24 and inlet valving means 22. Pumping means 28 include, but are not limited to, e.g., foreline pumps, turbomolecular pumps, vacuum pumps, rotary vane pumps, or other compatible pumps for i) pumping atmospheric, environmental, and/or gas sample(s) through manifold 20, and ii) maintaining desired operational vacuum or pressure into system 10, the pumping means 28 coupling to fractioning means 26. In one embodiment, fractioning means 26 is a 3-way connector (e.g., T-connector) or 3-way union coupled to a foreline vacuum pump (e.g., an Edwards model No. 12, available commercially from Scientific Instrument Services, Ringoes, N.J.; or, Alcatel model 2105 vacuum pump from Alcatel Vacuum Products, Annecy, France). No limitations are hereby intended.

Components of manifold 20 are fully conformational i) conforming (e.g., adapting) to parameters and/or event(s) associated with sampling environment 30, including, but not limited to, e.g., flow rates, clearance rates, and/or other parameters dynamically and collectively, and ii) introducing or metering samples conforming to the vacuum and/or operational pressure of, e.g., the mass-selective detector, component, and/or instruments comprising analysis/monitoring system 10. For typical samples taken from oxygen-rich atmospheric sampling environments, for example, inlet valving means 22 introduces atmospheric or other samples to system 10 at a flow rate that maintains the vacuum or operational pressure of the mass-selective detectors, components, and/or instruments comprising system 10. In particular, oxygen-rich samples are metered/introduced at a vacuum or other instrument specified pressure selected in the range from about $0.5 \times 10^{-5}$ Torr to about $5 \times 10^{-6}$ Torr relative to the operational requirements of the mass-selective detector, component, or instrument. More particularly, pressures are selected in the range from about $1.0 \times 10^{-5}$ Torr to about $2.0 \times 10^{-5}$ Torr relative to the operational requirements of the mass-selective detector, component, or instrument. Samples taken from oxygen-deficient or oxygen-poor sampling environments can be introduced at pressures up to about 706 torr (0.8 atm).

As will be appreciated by persons of skill in the art, various devices can be coupled to manifold 20 and/or incorporated as a component of systems 10 and/or 50 without limitation. For example, manifold 20 can be optionally equipped with a particulate trap 32, filter 32, or trapping system 32 inserted between fractioning means 26 and pump 28 for trapping particulates removed from the atmospheric or environmental samples for characterizing and determining origin (e.g., source) of particulates. Particulate traps include, but are not limited to, filtering traps, environmental traps, air quality traps, occupational health traps (e.g., VERT, BUWA, Suva, AUVA, TBG-certified), biological traps, oil mist eliminators, coated traps, molecular sieve traps, metal sieve traps, single-stage and multi-stage traps, cascade impactor traps, foreline traps, fiberglass traps, ceramic filter traps, glass-fiber traps (e.g., knitted glass), and the like. Coatings for coated traps include, but are not limited to, e.g., polytetrafluoroethylene (PTFE) also known as Teflon® (DuPont Corp., Wilmington, Del.), nylon (DuPont Corp., Wilmington, Del.), polyetheretherketone also known as PEEK® (Victrex USA, Greenville, S.C.), or other polymer. Filters include, but are not limited to, coarse, fine, membrane, or combinations thereof, e.g., a 47-mm in-line stainless steel particulate filter incorporating a combination coarse particulate filter and a fine user-selectable particulate membrane (Pall Corporation, East Hills, N.Y. 11548). Membrane filters include, but are not limited to, coated, selective response, pore-selective, reactive (e.g., for detection of biological agents), indicator, Nylasorb™, Zefluor™, Zylon™, Tissuquartz™, Emfab™, Fiberfilm™, GLA-5000™, or other membrane filters. Filtering provides characterization capabilities including, but not limited to, trapping of, e.g., acid rain (e.g., Nylasorb™, Zefluor™), aerosols (e.g., Tissuquartz™, Emfab™, Fiberfilm™), fibers (e.g., asbestos, including, e.g., GN-6 Metricel® and GN-4 Metricel® membranes), lead, dust (GLA-5000™ and DM Metricel® membranes), PM-rated particulates (e.g., PM-10, PM-2.5, etc.), polynuclear aromatic hydrocarbons (PAH), silica, other particulate classes, and combinations thereof.

Further, heating sources including, but not limited to, external, internal, fixed, chemical, organic, inorganic, gas, electrical, electromagnetic, electrochemical, solar, radiant, convection, or combinations thereof may be incorporated. Additionally, heating blankets, tapes, polymerase chain reaction (PCR-type) quick response heaters, elements, filaments, blowers, ovens, columns, beds, exchangers, thermal ramping heating devices, AC sources, DC sources, AC current/DC current sources, or combinations thereof may be incorporated. No limitations are intended.

Other devices including, but not limited to, e.g., ionization sources (e.g., ESI, MALDI, Glow-discharge, filaments, and the like), ion gauges, mass-flow controllers, gas sources, gas capture/desorption devices (thermal desorption tubes), probes including, but not limited to, temperature probes, humidity probes, relative wetness and total wetness monitoring probes, microsensors and microsensor arrays (e.g., for detection of biological agents, components including, but not limited to, e.g., production-dependent components, allied components, metabolic end-products and components, and/or residues), or other devices may be coupled with manifold 20 and/or incorporated for sample handling, control, and/or analysis. For example, a combination temperature/humidity and/or wetness monitoring probe (e.g., Sensatronics Environmental Sensing, Bow, N.H. 03304) can be coupled between manifold 20 and sampling environment 30 for collecting temperature, humidity, and/or wetness data regarding an environmental sampling event in real-time. No positioning limitations are intended.

Sample handling, control, and/or analysis may further be performed in conjunction with computers and/or computer-interfaced devices. For example, various system, analysis, and/or apparatus components may be operated in conjunction with computer and/or process/control software (e.g., MS Sensor Process Analysis Software, Diablo Analytical, Inc., Concord, Calif., http://www.diab.com), or other commercially available control software (e.g., National Instruments Corporation, http://www.ni.com) for controlling various and multiple instruments, computers, and/or digital instrumental components including, but not limited to, e.g., opening/closing of valves, inputting/changing settings and operating parameters, sample metering, setting/inputting/changing pressures, temperatures, flow rates, thermal ramping, heating, and/or other associated parameters for systems 10 and/or 50. No limitations are hereby intended.

Figure 3:
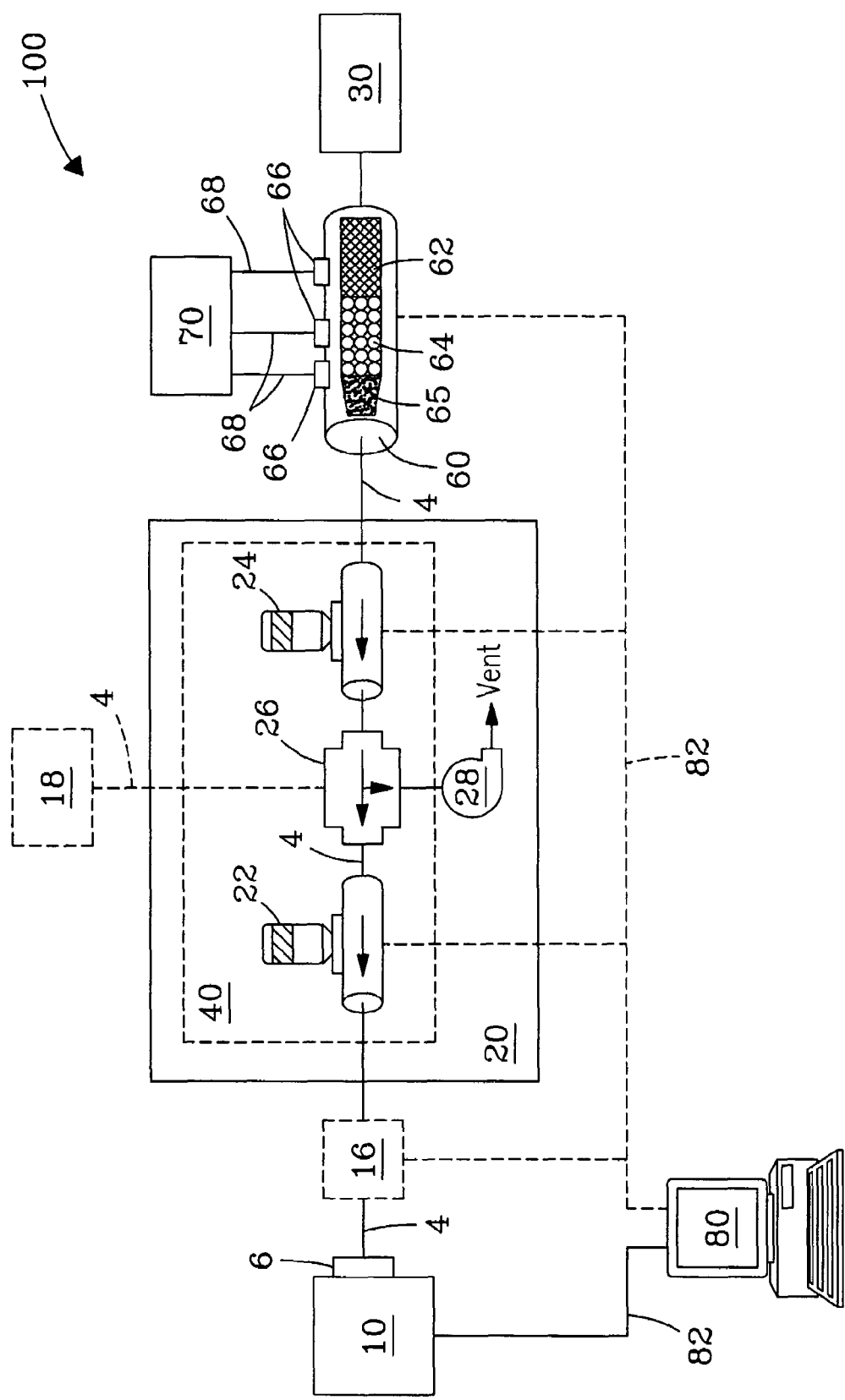
FIG. 3 illustrates a conformational manifold of the invention for monitoring and/or analysis of samples from an atmospheric gas sampling environment in real-time, according to a further embodiment of the invention.

FIG. 3 illustrates a system 100 for monitoring and/or analysis of samples from an atmospheric or environmental sampling environment 30 in real-time, according to another embodiment of the invention. System 100 comprises a fully conformational manifold 20 configured with an optional heating source 40 (e.g., heating blanket or tape) for heating manifold 20, and/or heating samples introduced to analysis/monitoring system 10. An optional ionization source 16 (e.g., a glow discharge source) is further incorporated permitting an MS/MS-type mode for MS detector monitoring/analysis in conjunction with system 10. Further incorporated is an optional gas source 18 coupled to manifold 20, e.g., via fractioning means 26 (e.g, via a 4-way connector) for introducing, e.g., a chemical ionization gas to samples introduced to analysis system 10. No limitations are hereby intended. For example, in a sampling environment 30 containing multiple sample analytes/constituents of interest with, e.g., overlapping mass profiles but different desorption profiles, analytes can be analyzed in conjunction with, e.g., desorption tubes that capture and concentrate analytes, and a thermal ramping heating system for specific timed and/or programmed release of analytes to analysis system 10. For example, as illustrated in FIG. 3, a selective-elution device 60 (e.g., stainless steel sleeve) is incorporated for multi-component concentration, desorption, and temperature dependent release of a multiplicity of analytes collected from sampling environment 30. As illustrated, device 60 comprises a capture zone 62 coupled to desorption zone 64 further coupled to concentrator/focusing zone 65. Capture zone 62 is filled with a sorbent (e.g., activated carbon) or other capturing material chemically coupled to a thermal desorption material (e.g., siloxane or other chromatographic material) in zone 64 for selectively desorbing compounds/analytes, further coupled to a concentrating material (e.g., deactivated silica) in zone 65 for concentrating eluted compounds/analytes prior to introduction to manifold 20. Release of individual analytes to manifold 20 with ultimate introduction into a mass-selective (MS) detector, component, or instrument of system 10 is done in conjunction with, e.g., temperature controlled (e.g., ramping) heating sources 66 (e.g., a PCR-type quick response heater), linked electrically to a power source (e.g., a variac or AC/DC current source) 70 by electrical means 68 (e.g., electrical wire) allowing for temperature dependent, multi-component and/or co-eluting compound desorption and release for multi-component compound/analyte monitoring, detection, and/or analysis. Regeneration of sorbent in capture zone 62 may be effected by closing inlet valve 22 stopping flow to system 10 and opening throughput valve 24 to a maximum flow while ramping temperature of device 60 in conjunction with heaters 66. Components of system 100 are further optionally controlled as described herein in conjunction with a computer 80 and control means 82 (e.g., wireless, GPIB, DAQ, PXI, control software, or other control means). All devices and configurations as will be implemented by those of skill in the art are within the scope of the present invention. No limitations are hereby intended.

Figure 4:
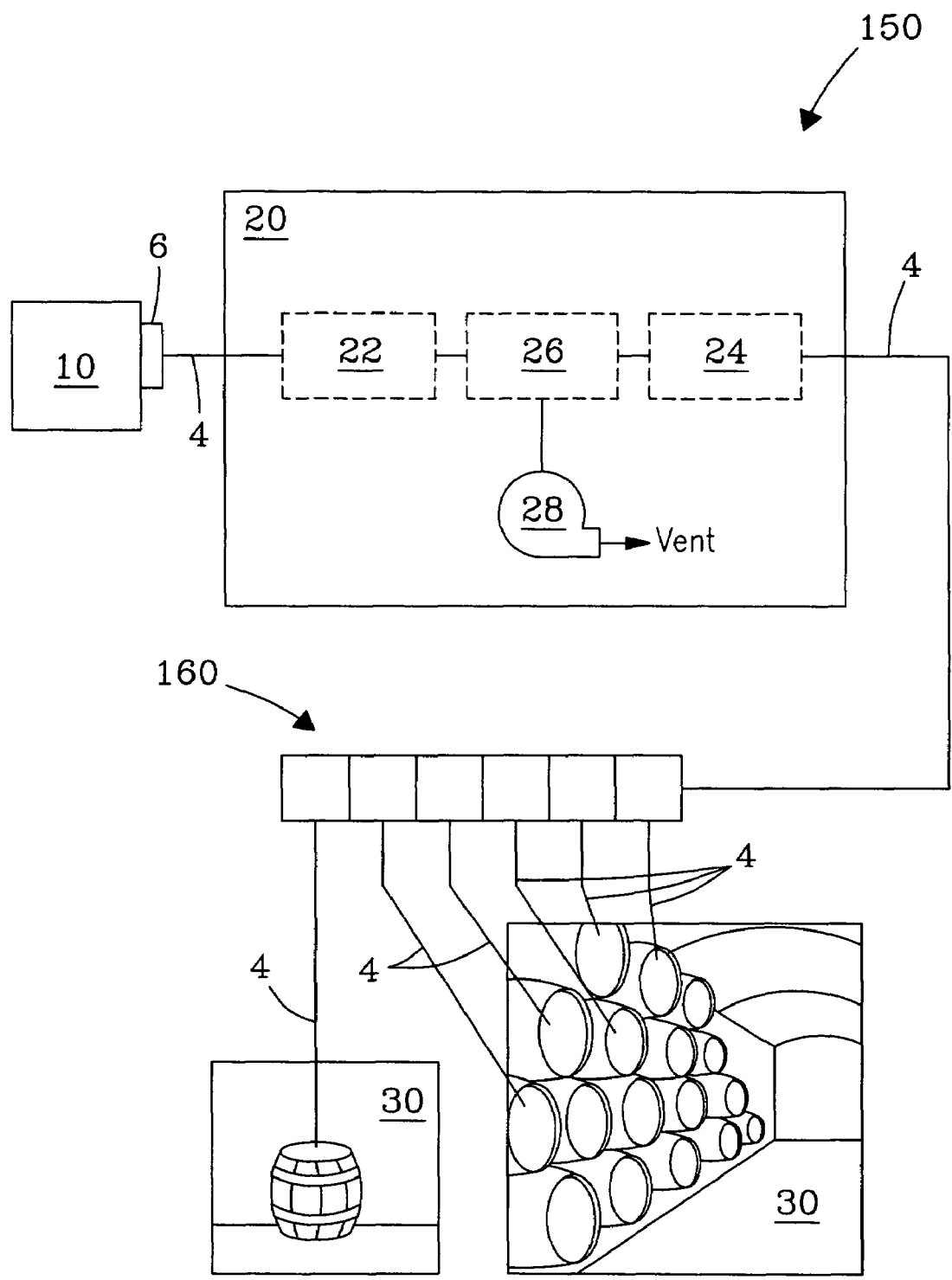
FIG. 4 illustrates a system for real-time monitoring/analysis of volatile and/or semi-volatile organics present in sampling environments having a head space or volume, according to a further embodiment of the invention.

FIG. 4 illustrates a system 150 for monitoring and/or analysis of samples from an atmospheric gas sampling environment 30 in real-time, according to another embodiment of the invention. System 150 is configured for monitoring/analysis of headspace volumes associated with fermentation processes, e.g., in a brewery or winery wherein volatile and/or semi-volatile organics are detected. Sampling environments 30 associated with such processes, include, e.g., head space volumes of various storage vessels, tanks, wells, chambers, containers, or the like. As illustrated in the figure, system 150 couples to a sampling environment 30 comprising a single storage barrel or a multiplicity of storage barrels, each barrel having a respective head space or volume linked via a single or a series of position-switchable valve(s) 160 (e.g., Cheminert® valves from Valco Instruments Co. Inc., Houston, Tex. 77255, http://www.vici.com) to manifold 20. Various analytes of interest including, but not limited to, e.g., alcohols, aldehydes, and/or aromatics, are subsequently monitored, and/or analyzed in conjunction with a mass-selective detector, component, or instrument in analysis system 10. In but one example, manifold 20 throughput rate (e.g., via throughput valve 24) is manually or digitally set to a low value, e.g., 1-3 mL/min, conforming with the low headspace volume or generated pressure. Alternatively, system 10 may be correlation calibrated for an expected analyte concentration in conjunction with, e.g., a low part-per-billion (ppb) liquid sample taken from each barrel over time and analyzed by standard analytical or wet chemistry methods. Release response within the headspace volume can thus be correlated with concentrations for desired analyte(s), e.g., ethanol or aldehydes, in the liquid as a function of time, temperature, headspace volume, concentrations, and/or other associated parameters. The instant embodiment is not intended to be limiting. For example, manifold 20 and its associated components may be operated in conjunction with computers and/or software for controlling various operations and parameters, including, but not limited to, flow rates, pressures, temperatures, heating, opening/closing of valves, as described herein. All such control and/or analysis options as will be envisioned by those of skill in the art are hereby incorporated.

Figure 5A:
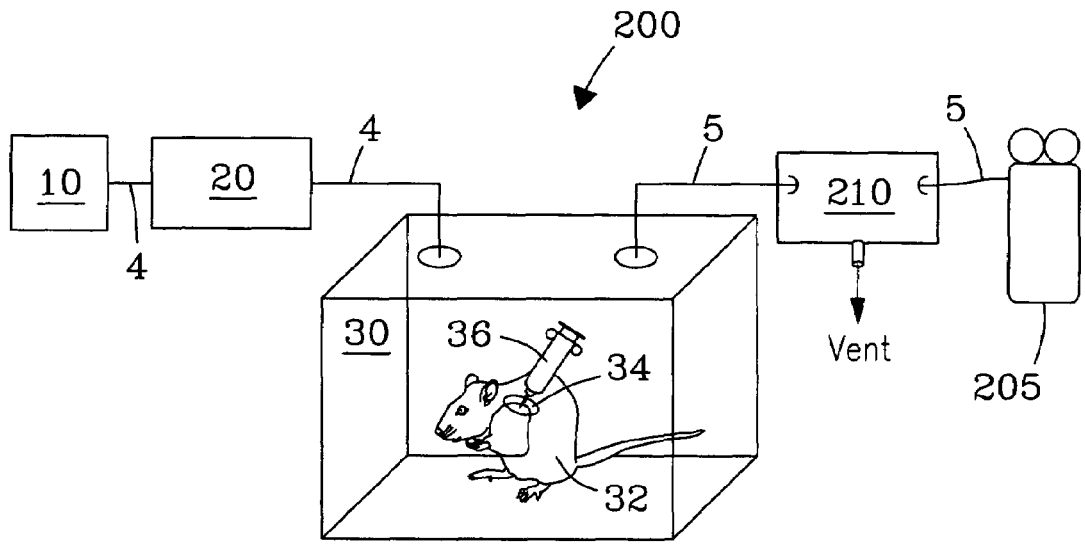
FIG. 5a illustrates a system for real-time monitoring/analysis of analytes released to a sampling environment in conjunction with animal exposure studies, according to another embodiment of the invention.

FIG. 5a illustrates a system 200 for real-time monitoring and/or analysis of analytes released to a sampling environment 30 in conjunction with animal exposure studies, according to another embodiment of the invention. In Example 4 below, a live animal (e.g., rat) 32 placed in a sampling environment 30 is dosed or treated with a chemical or a drug delivered, e.g., via a dermal cup bulb 34 in conjunction with a precision syringe 36 or other delivery means, including but not limited to, dermal patch, injection, or the like. Environment 30 is monitored in real-time via coupling with manifold 20 at the breathing (clearance) rate of the animal until desired target analytes, metabolites, and/or chemical indicators of interest are detected or quantified in the mass-selective detector or instrument comprising system 10. Time from chemical or drug exposure to detection of target analytes may be correlated, e.g., with human exposure models.

Figure 5B:
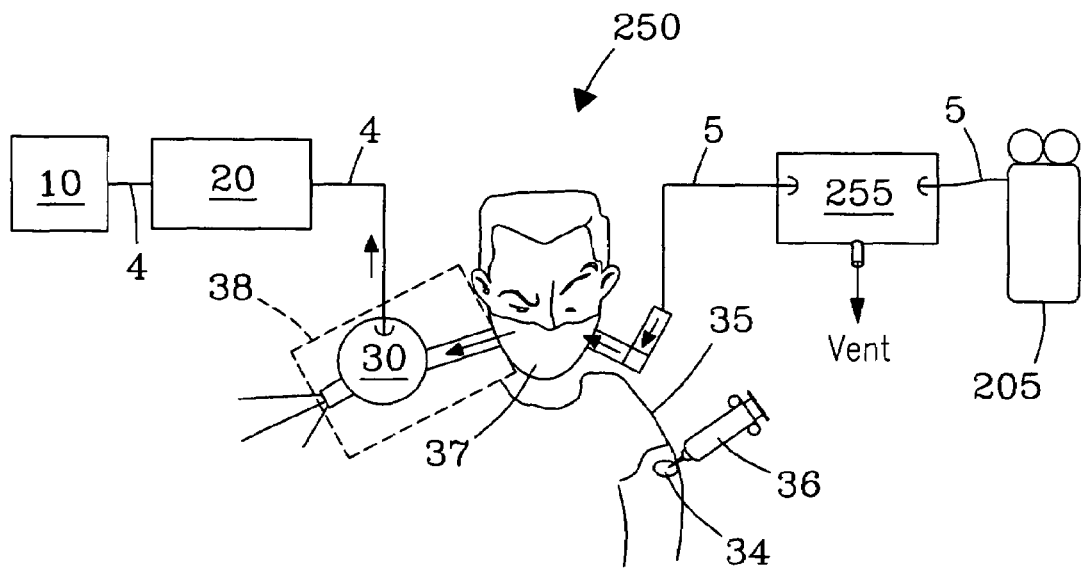
FIG. 5b illustrates a system for real-time monitoring/analysis of analytes released to a sampling environment in conjunction with human exposure studies, according to another embodiment of the invention.

In another embodiment of the invention illustrated in FIG. 5b, a system 250 is configured for real-time monitoring and/or analysis of analytes in a sampling environment 30 in conjunction with human exposure studies. As illustrated in the figure, a human subject 35 breathes into sampling environment 30 comprising a mask 37 and breathing tube 38 filling the sampling environment 30 (e.g., 3-L glass sampling bulb) with exhaled air. Mask 37 and tube 38 are further coupled via tubing 5 to a high-purity air source 205 supplying breathing air to human subject 35 through a flexible gas bag 255 (e.g., a 100-L Tedlar® bag made of polyvinyl fluoride, Dupont, Wilmington, Del., available commercially from Cole-Palmer Instrument Company, Vernon Hills, Ill.) introduced to prevent backflow to manifold 20. Drugs or chemicals are delivered, e.g., via a dermal cup bulb 34 in conjunction with a precision syringe 36 or other delivery means, including but not limited to, dermal patch, injection, or the like through the skin of human subject 35. Environment 30 is monitored in real-time via coupling with manifold 20 at a throughput rate conforming to the breathing (clearance) rate of subject 35 until desired target analytes, metabolites, and/or chemical indicators of interest are detected or quantified in the mass-selective detector or instrument of system 10. Time from chemical or drug exposure to detection of target analytes may, e.g., be correlated with models for human exposure and/or tolerances. Other similar environmental or toxicological studies as will be contemplated by those of skill in the art are within the scope of the present invention, e.g., in leak testing of personal protection equipment including, but not limited to, self-contained breathing equipment, masks, medical suits, clothing, and the like. No limitations are intended.

Figure 6:
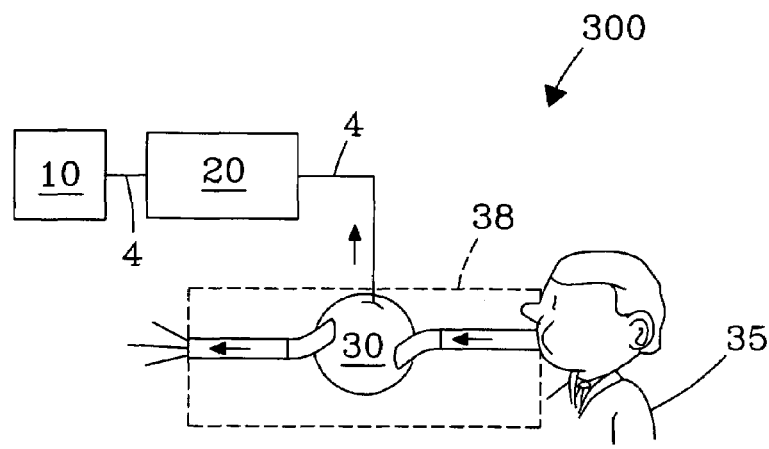
FIG. 6 illustrates a system for real-time monitoring and/or analysis of breath biomarkers correlated with determination of metabolic states, fitness states, disease states, according to another embodiment of the invention.

FIG. 6 illustrates a system 300 for real-time monitoring and/or analysis of breath biomarkers correlated with determination of metabolic states (e.g., inebriation), fitness states, disease states (e.g., cancer, ketosis), and the like, according to yet another embodiment of the invention. In but one example, a breathing tube 38 comprises a sampling environment 30, e.g., a 3-liter sampling bulb or volume 30 as detailed by Gordon et al. (*Environmental Health Perspectives*, 110, No. 7, Jul. 2002, pp. 689-698), whereby large sample aliquots can be withdrawn without creating a significant backflow. In the instant embodiment, breathing tube 38 has a 1.5 inch I.D. and a length of about 3 feet, but is not limited thereto. Volume 30 (sampling environment) is coupled via, e.g., ¼-inch tubing 4 to manifold 20. Test subject 35 exhales into tube 38 filling volume 30. Volume 30 is sampled at a throughput rate conforming with the breathing (clearance) rate (e.g., 200 mL/min) of subject 35, whereby target analytes, metabolites, and/or desired indicator chemicals are monitored, analyzed, and/or quantified in analysis system 10 comprising, e.g., a mass-selective detector, component, or instrument whereby analytical data are provided for appropriate treatment options, and/or further decision-making. In an example, state of inebriation can be assessed by monitoring for alcohols in exhaled breath. In another example, state of fitness can be determined by measuring oxygen content in exhaled breath as a function of, e.g., time in training, (e.g., over a period of, e.g., 6 weeks), a decreasing oxygen content in the exhaled breath over time being one measure correlated with a state of fitness. Alternatively, state of fitness can be assessed by measuring percent $CO_2$ in exhaled breath as a function of, e.g., time in training as a measure of clearance efficiency. In a final illustrative example, disease states, e.g., diabetes, can be identified by monitoring specific analytes, e.g., ammonia, ketones, acetones, or other metabolites in exhaled breath. Likewise, cancer can be identified by monitoring specific biomarker and/or metabolic offgasses in exhaled breath. No limitations are hereby intended.

Figure 7:
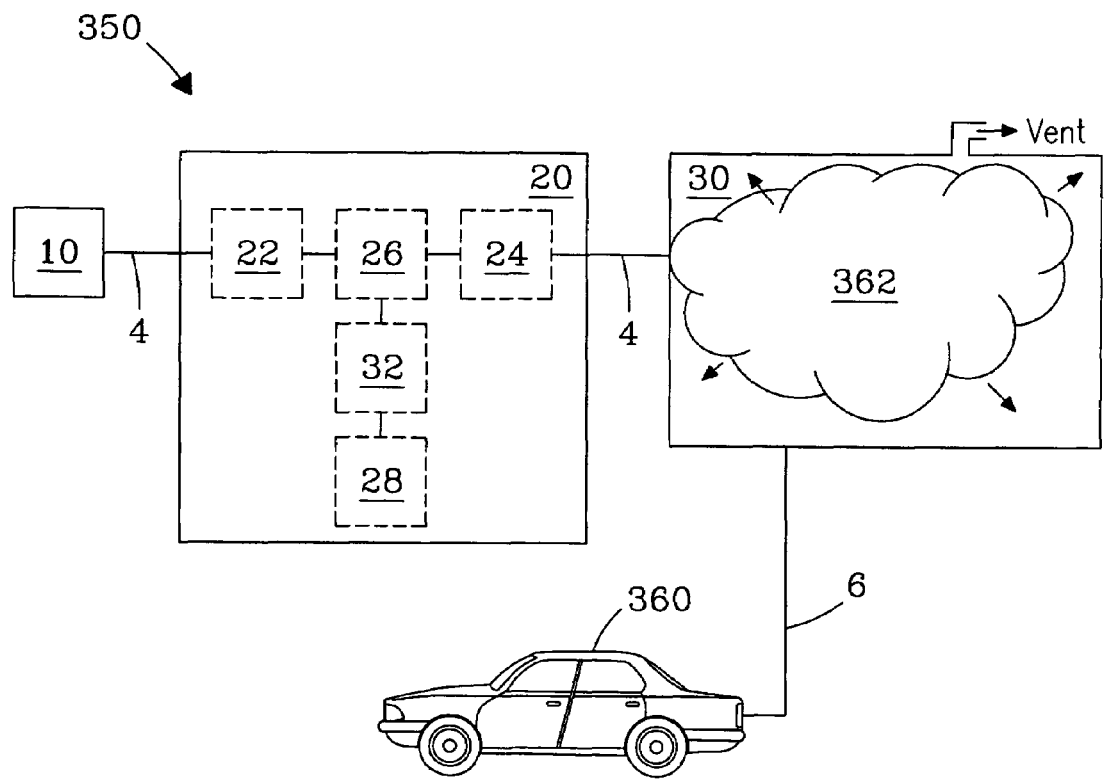
FIG. 7 illustrates a system for conformational real-time monitoring/analysis of analytes released to a sampling environment in conjunction with exhausting or offgassing systems (e.g., vehicle emissions), according to another embodiment of the invention.

FIG. 7 illustrates a system 350 for real-time sampling, monitoring and/or analysis of analytes released to a sampling environment 30 in conjunction with exhausting and/or offgassing systems, according to another embodiment of the invention. In the instant embodiment, system 350 is configured for monitoring, testing, and/or analysis of vehicle emissions. In the figure, sampling environment 30 is filled, via suitable piping or conduit means 6, with exhaust 362 generated by vehicle 360 and introduced via tubing 4 to manifold 20, i.e., via throughput valve 24 at a throughput rate conforming (e.g., not exceeding) the generation rate of exhaust 362 into sampling environment 30. Samples containing volatile and semi-volatile analytes are subsequently metered via inlet valve 22 to analysis system 10 at a flow rate conforming to the operational vacuum and/or pressure of system 10 and/or its components, as described herein. In the instant embodiment, manifold 20 is configured with a particulate trap 32 (e.g., a Teflon®-coated fiberglass filter, Pall Corporation, East Hills, N.Y. 11548) incorporated between fractioning means 26 and pumping means 28 for trapping particulates removed from the exhaust samples. Particulate trap 32 can be used in conjunction with characterization of collected particulates, as described herein, including, but not limited to, e.g., total particulates (e.g., quantities), particulate size(s), particulate generating sources, emission pollutants, organic fractions, e.g., soluble organic fractions (SOF), volatile organic fractions (VOF), inorganic fractions (e.g., soluble), and the like, and/or other parameters. Emission pollutants include, but are not limited to, e.g., CO, hydrocarbons, $NO_x$, can also be similarly performed. Any volatile and/or semi-volatile chemical(s) and/or analyte(s) can be monitored and/or quantified as will be understood by those of skill in the art. No limitations are hereby intended. Various analyses are performed with parameters correlated with quantity of atmosphere or environment processed including, e.g., flow rates of throughput valve 24 (e.g., 400 ml/min) and duration of sampling. Concentration (or apparent density) of particulate matter can be gravimetrically determined from equation [1]:

$$C = \frac{P}{V} \quad [1]$$

where C is the concentration of particulate matter in the sample (e.g., in mg/m³), P is the quantity of particulate matter obtained by difference before and after sampling (e.g., in mg), and V is the volume of atmosphere or environment sampled (e.g., in m³).

All offgassing, exhausting, emission, and/or environmental analyses as will be contemplated by those of skill in the art are within the scope of the invention. For example, manifold 20 may be configured for real-time measuring and monitoring of effluent streams in conjunction with EPA environmental release limits, e.g., stack releases, diesel emissions, opacity measurements, $SO_x$ emissions, and the like. In yet another embodiment, manifold 20 can be configured for testing of room air quality, e.g., in enclosed or crowded meeting rooms where, e.g., oxygen depletion or noxious concentrations of carbon dioxide can exist. No limitations are hereby intended.

Figure 8A:
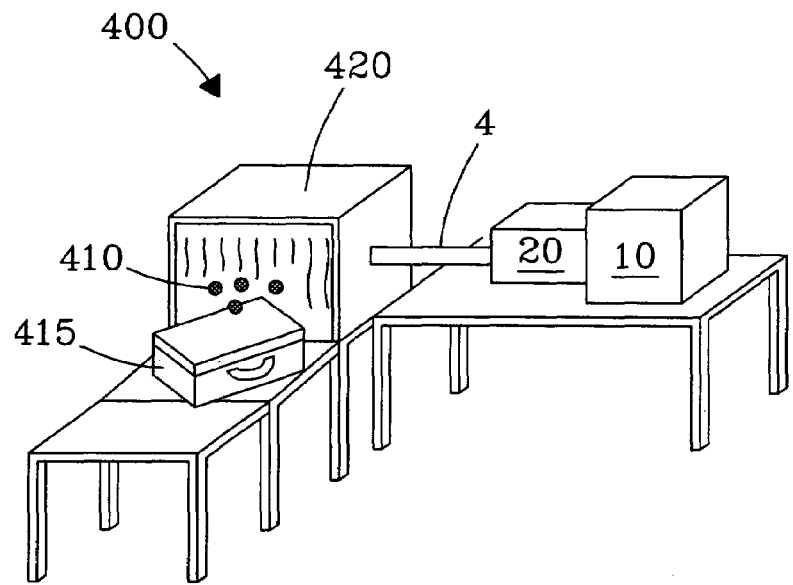
FIG. 8a illustrates a system for real-time measurement of hazardous chemical and biological agents concealed in luggage, cargo, and like containment for transporting to remote locations, according to another embodiment of the invention.
Figure 8B:
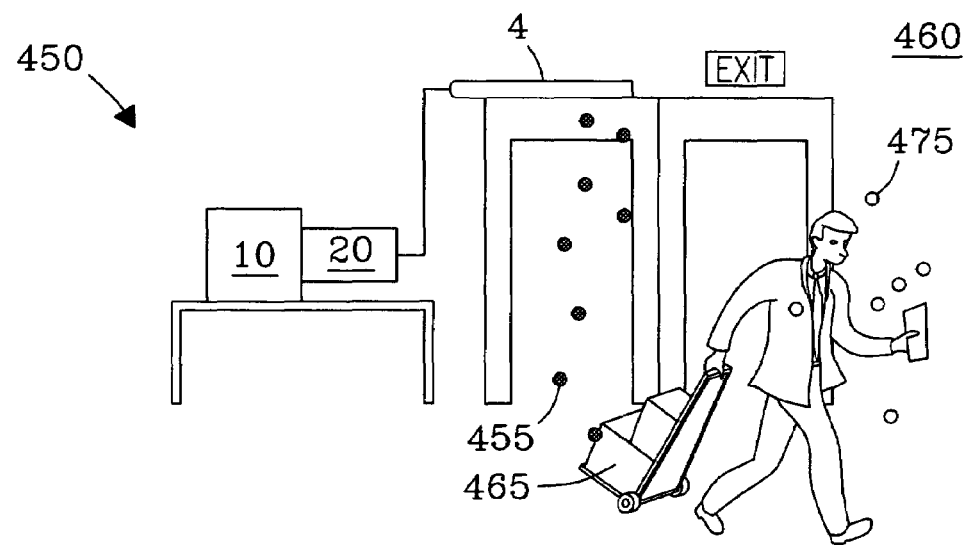
FIG. 8b illustrates a system for real-time monitoring/analysis of analytes released to a sampling environment in conjunction with offgassing and/or exhausting systems (e.g., vehicle emissions), according to another embodiment of the invention.

FIG. 8a illustrates a system 400 for real-time measurement of concealed hazardous chemical and biological agents 410, e.g., in luggage 415, cargo, and or other containers employed for transporting agents 410 to remote locations, according to another embodiment of the invention. In the instant embodiment, system 400 is configured for detection of hazardous chemical and biological agents 410 concealed, e.g., in luggage 415. Manifold 20 is coupled to, e.g., an airport X-ray scanning device 420 (sampling environment) via conduit or piping 4 introducing any hazardous chemical and/or biological agents 410 collected from the sampling environment to manifold 20, metering samples to system 10 for detection and/or analysis. FIG. 8b illustrates a similar system 450 for detection of concealed toxic and/or hazardous chemical and biological agents 455 transported or carried into public buildings (e.g., airports, shopping centers, office buildings, etc.) where people congregate. In the figure, system 450 comprises a mass-selective analysis system 10 coupled to manifold 20. Manifold 20 is further coupled to a sampling environment 460, e.g., an open air space near a doorway, via conduit 4, introducing hazardous chemical and/or biological agents 455 collected from the sampling environment 460 into manifold 20 and to system 10 for detection and/or analysis. In the instant embodiment, system 450 can detect volatile and/or semi-volatile hazardous chemical and biological agents 455 including components thereof, released, e.g., from containers 465, packages, clothing 475, or other sources.

Figure 9:
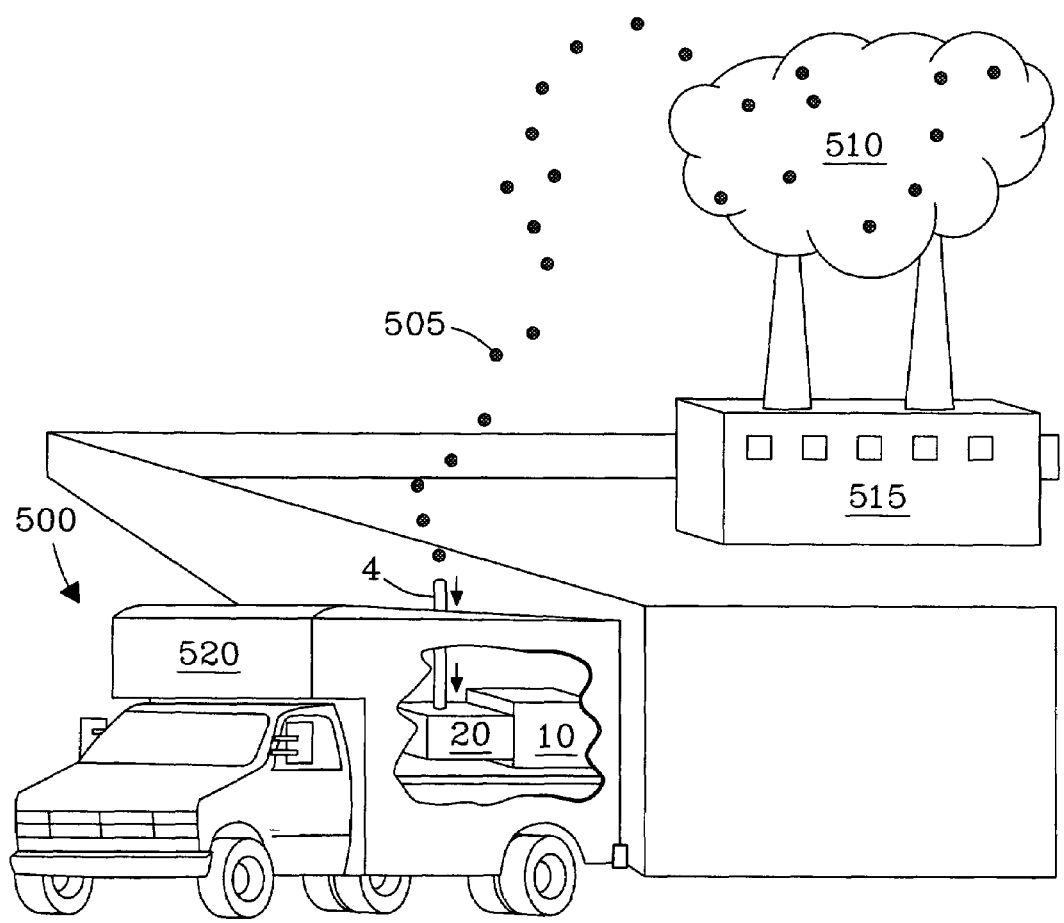
FIG. 9 illustrates a system for real-time measurement of hazardous chemical and biological agents associated with, e.g., terrorist activities, weapons manufacturing, enrichment of fissionable materials, and the like, according to another embodiment of the invention.

FIG. 9 illustrates a system 500 of a mobile design for detection of hazardous chemical and biological agents 505 and/or components thereof, as described herein, released into a sampling environment 510 near, e.g., chemical and/or biological weapons and/or enrichment facilities 515. In the instant embodiment, manifold 20 is configured with a particulate trap (e.g., reactive membrane) (not shown) for trapping particulates present in emission exhausts and a sensor array as described previously herein (not shown) for detection of biological agents, production-dependent components, allied components, metabolic end-products and components, and/or residues, incorporated between fractioning means 26 and pumping means 28. In the figure, system 500 comprises a mass-selective analysis system 10 coupled to a manifold 20, wherein the manifold 20 and analysis system 10 is located in a vehicle 520 allowing transportation to a remote location for measuring and monitoring of sampling environment 510. Manifold 20 samples environment 510, e.g., analytes dispersed or released near a manufacturing facility 515, via conduit 4, introducing hazardous chemical and biological agents 505 to manifold 20 and to system 10 for detection and/or analysis. Throughput is chosen at a rate that maximizes sensitivity for the target analyte depending on the selected sampling environment. For example, as will be recognized by those of skill in the art, concentrations of analytes present in environmental plumes released from a manufacturing facility will depend at least in part on the dispersal rates relative to such factors as wind velocities, direction, high concentrations, or other associated factors.

A greater understanding of the invention and applications will be understood by reference to the following examples.

EXAMPLE 1

Example 1 details calibration of analysis system 10 in preparation for monitoring, detection, and/or analysis of samples from a sampling environment 30, in conjunction with manifold 20, in real time.

Figure 10:
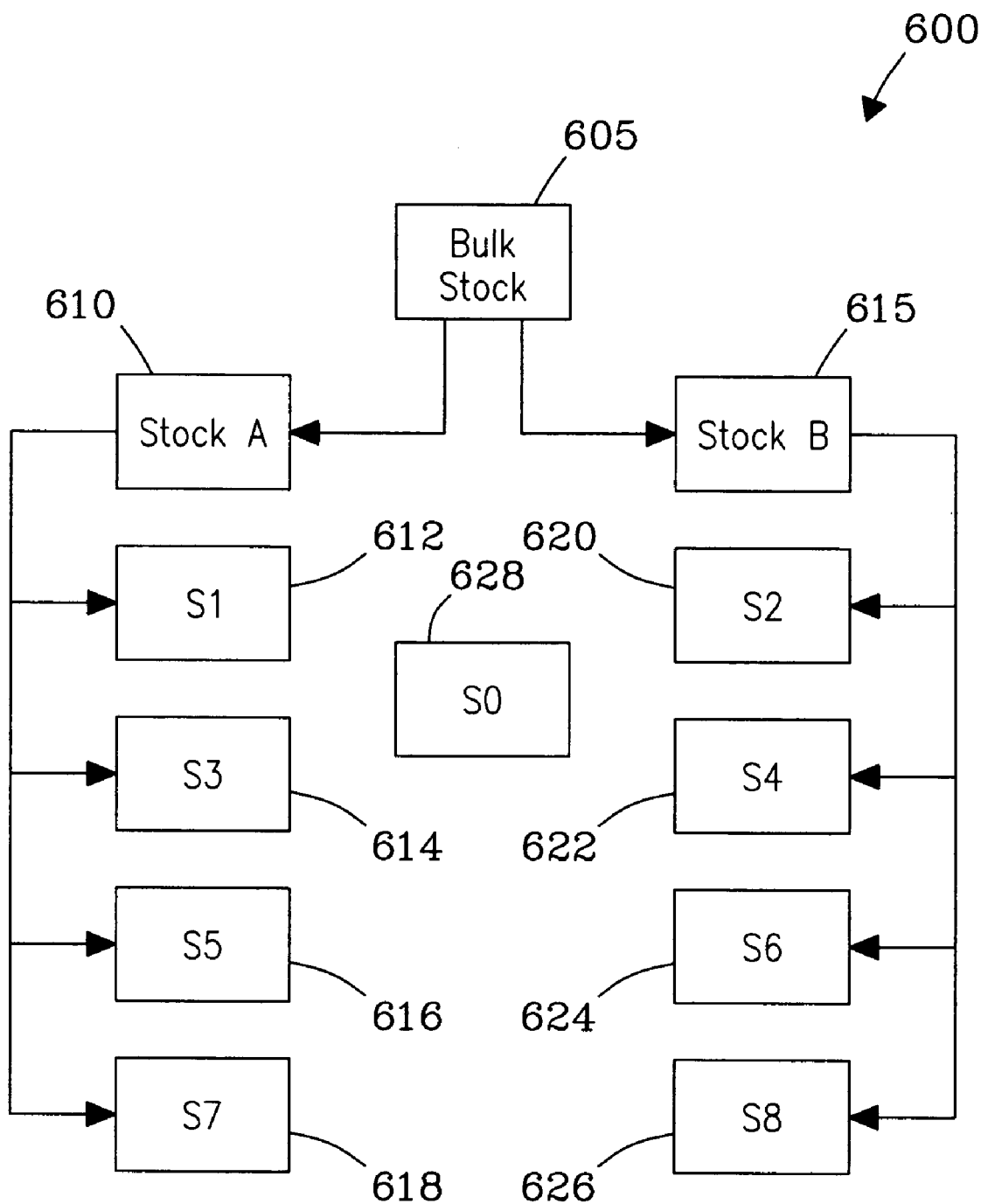
FIG. 10 illustrates a process for preparing precision dilution standards for calibrating the mass-selective instrument system in preparation for monitoring, detection, and/or analysis of samples collected from a sampling environment in conjunction with the sampling apparatus of the invention, in real time.

FIG. 10 illustrates a process 600 for preparing precision air-chemical dilution standards for calibrating system 10 at concentrations in a range expected for the analyte(s) of interest from sampling environment 30. In the figure, a bulk stock 605 is prepared by introducing, e.g., 2 liters of high-purity air via precision syringe (e.g., Hamilton USA, Reno, Nev. 89520-0012) or other delivery system (e.g., pressure regulator) into a sampling bag (e.g., a 3 liter Tedlar® sampling bag, available commercially from Cole-Palmer Instrument Company, Vernon Hills, Ill.) and introducing a known quantity of a reference material (e.g., 0.5 µL of, e.g., 99.9% toluene (density =0.865 g/mL), Sigma-Aldrich, St. Louis, Mo.)) via septum or valve into the bag and gently agitating until the liquid vaporizes and mixes uniformly, the concentration (57,571.22 ppb) being given by equation [2]:

$$[\text{Bulk stock}] = [(\mu L \text{ injected}/2000)*(\rho)*(R)*(M.W.)*(10E9)] \quad [2]$$

where "ρ" is the density (g/mL) of the reference chemical, "R" is the gas constant (e.g., 24.53 mol/L), "M.W." is the molecular weight of the reference material (e.g., 92 g/moL for Toluene), "bulk stock" is the concentration of bulk mixture 605. Separate chemical mixture stocks, e.g., Stock A 610 and Stock B 615, are prepared by introducing, e.g., 1800 mL and 1900 mL, respectively, of high-purity air into respective sampling bags for Stock A 610 and Stock B 615 into which, e.g., 200 mL and 100 mL of the bulk stock mixture 605, respectively, is introduced and mixed, yielding relative concentrations for Stock A 610 and Stock B 615 of, e.g. 5757 ppm and 2879 ppm.

Dilution standards for calibration are then prepared as illustrated in FIG. 10. Two sets of calibration samples are illustrated, but are not limited thereto. A first set of standards including, e.g., standards S1 612, S3 614, and S5 616, S7 618 is prepared by introducing, e.g., ~2 liters of high-purity air (less the quantity of stock mixture to be introduced) via precision (e.g., gas-tight) syringe to respective sample bags and introducing e.g., 2 mL, 50 mL, 400 mL, and 1000 mL, respectively, of Stock mixture A 610 into each. A second set of dilution standards, e.g., standards S2 620, S4 622, S6 624, and S8 626, is prepared similarly by injecting, e.g., 10 mL, 75 mL, 400 mL, respectively, of Stock mixture B 615 into respective sample bags containing ~2 liters of high-purity air (less the quantity of stock mixture to be introduced) and mixing, the concentrations for each dilution sample being given from equation [3]:

$$[\text{Dilution Sample}] = (\text{Stock } A \text{ or } B \text{ conc.})/(\text{dilution factor}) \quad [3]$$

where "Stock A or B conc." is the concentration of either Stock A or Stock B (e.g., 5757 ppm and 2879 ppm) and "dilution factor" is the ratio of the total high-purity air volume in the final mixture (e.g., 2000 mL) divided by the volume of Stock A or B introduced to prepare the dilution sample (e.g., 400 mL for Sample S5), yielding a dilution factor of 5 (2000 mL/400 mL). Any number of standards within the range expected for the analyte(s) of interest can be prepared separately or in analyte combinations. In addition, standards can be prepared at the same and/or different concentrations permitting precision and/or accuracy checking. Further, standards containing no reference material, e.g., "blank" samples (S0) 628 can be prepared for purposes of mass-spectrometric background correction. Table 1 lists concentrations (calculated and experimental) for toluene standards (S1 through S10) prepared from Stock Mixture A 610 and Stock mixture B 615.

TABLE 1

Concentrations calculated for dilution standards prepared from Stock mixtures A and B for calibration of a real-time instrument system.

| Dilution Standard | Qty, Stock A (cc)* | Qty, Stock B (cc)** | HP air, volume (cc) | Dilution Standard (ppb) ◊ |
|---|---|---|---|---|
| S0 | 0.00 | 0.00 | 2000 | 0.00 |
| S1 | — | 2 | 1998 | 2.88 |
| S2 | 10 | — | 1990 | 28.79 |
| S3 | — | 50 | 1950 | 71.96 |
| S4 | 75 | — | 1925 | 215.89 |
| S5 | — | 400 | 1600 | 575.71 |
| S6 | 400 | — | 1600 | 1151.42 |

TABLE 1-continued

Concentrations calculated for dilution standards prepared from Stock mixtures A and B for calibration of a real-time instrument system.

| Dilution Standard | Qty, Stock A (cc)* | Qty, Stock B (cc)** | HP air, volume (cc) | Dilution Standard (ppb) ◊ |
|---|---|---|---|---|
| S7 | — | 1000 | 1000 | 1439.28 |
| S8 | 1000 | — | 1000 | 2878.56 |

*Stock A: 1800 cc air + 200 cc bulk stock mixture to sample bag = 5757.12 ppb.
**Stock B: 1900 cc air + 100 cc bulk stock mixture to sample bag = 2878.56 ppb.
◊ concentration values (calculated).

EXAMPLE 2

Example 2 presents results from mass-spectrometric analysis of (o-xylene) gas calibration standards prepared in high-purity air analyzed in conjunction with manifold 20 and analysis system 10. Samples were prepared as described in Example 1. Tables 2 and 3 list data for intensity and concentration of o-xylene based on detection of a daughter product (m/z=91) analyzed in conjunction with the invention in real-time.

TABLE 2

Analysis (m/z = 91) results for o-xylene calibration standards, prepared in high purity air.

| Scan Time (min) Mass 91 | Blnk 0 | Std. 1 Value | Std. 2 Value | Std. 3 Value | Std. 4 Value | Std. 5 Value | Std. 6 Value | Std. 7 Value | Std. 8 Value | Std. 9 Value | Std. 10 Value |
|---|---|---|---|---|---|---|---|---|---|---|---|
| 0.51667 | 56 | 175 | 102 | 219 | 248 | 636 | 804 | 1090 | 2321 | 4749 | 90360 |
| 0.55000 | 90 | 94 | 80 | 176 | 162 | 519 | 1024 | 1231 | 2673 | 5485 | 88472 |
| 0.58333 | 85 | 76 | 118 | 273 | 295 | 620 | 895 | 1356 | 2071 | 5177 | 87312 |
| 0.61667 | 47 | 67 | 74 | 174 | 140 | 523 | 905 | 1281 | 2891 | 4737 | 90168 |
| 0.65000 | 67 | 69 | 182 | 279 | 202 | 590 | 1025 | 986 | 1943 | 5260 | 84544 |
| 0.68333 | 51 | 59 | 129 | 124 | 127 | 341 | 1038 | 1202 | 2383 | 5735 | 91368 |
| 0.71667 | 107 | 88 | 59 | 182 | 266 | 761 | 862 | 1085 | 1932 | 4943 | 88144 |
| 0.75000 | 31 | 80 | 164 | 26 | 226 | 526 | 884 | 1001 | 2182 | 4908 | 88496 |
| 0.78333 | 95 | 149 | 112 | 387 | 315 | 658 | 903 | 1040 | 2803 | 5366 | 89472 |
| 0.81667 | 52 | 46 | 46 | 124 | 152 | 902 | 590 | 1371 | 2567 | 4920 | 88352 |
| 0.85000 | 148 | 95 | 145 | 150 | 37 | 344 | 716 | 1186 | 2309 | 5406 | 90416 |
| 0.88333 | 83 | 78 | 19 | 158 | 227 | 563 | 1172 | 1473 | 2206 | 4975 | 87360 |
| 0.91667 | 181 | 175 | 161 | 175 | 156 | 754 | 1022 | 1009 | 2350 | 5058 | 92640 |
| 0.95000 | 135 | 21 | 143 | 309 | 224 | 494 | 1123 | 1328 | 2420 | 5248 | 93584 |
| 0.98333 | 64 | 49 | 94 | 286 | 396 | 631 | 1013 | 1134 | 2357 | 5125 | 89976 |
| 1.01667 | 82 | 181 | 92 | 243 | 298 | 693 | 905 | 1505 | 2082 | 4812 | 91176 |
| Average | 85.9 | 93.9 | 107.5 | 205.3 | 216.9 | 597 | 930 | 1,204 | 2,343 | 5,119 | 89,490 |

TABLE 3

Analysis (m/z = 91) results for o-xylene dilution standards prepared from stock mixtures for calibration of a real-time instrument system.

| Dilution Standard | Conc. (ppb) ◊ | Intensity (m/z)* | Bkg. Sub. (m/z = 91) | Conc. (ppb) ◊ ◊ | % Analyzed ◊ ◊ |
|---|---|---|---|---|---|
| S0 (Blank) | 0.00 | 86 | 0.00 | −6.6 | n/a |
| S1 | 2.51 | 94 | 8.00 | 2.6 | 102.98 |
| S2 | 25.13 | 108 | 21.63 | 18.2 | 72.46 |
| S3 | 62.82 | 205 | 119.44 | 130.4 | 207.55 |

TABLE 3-continued

Analysis (m/z = 91) results for o-xylene dilution standards prepared from stock mixtures for calibration of a real-time instrument system.

| Dilution Standard | Conc. (ppb)◊ | Intensity (m/z)* | Bkg. Sub. (m/z = 91) | Conc. (ppb)◊◊ | % Analyzed◊◊ |
|---|---|---|---|---|---|
| S4 | 188.45 | 217 | 131.06 | 143.7 | 76.26 |
| S5 | 502.52 | 597 | 511.31 | 579.8 | 115.38 |
| S6 | 1,005.04 | 930 | 844.19 | 961.5 | 95.67 |
| S7 | 1,256.63 | 1,205 | 1,119.00 | 1,276.7 | 101.60 |
| S8 | 2,512.61 | 2,343 | 2,257.25 | 2,582.0 | 102.76 |
| S9 | 5,025.22 | 5,119 | 5,033.13 | 5,765.4 | 114.73 |
| S10 | 50,252.19 | 89,490 | 89,404.13 | 102,552.1 | 204.02 |
| [m] = | 1.15E+00 | | [b] = | −6.6E+00 | |

◊Calculated values from stock mixtures, prepared as described in Example 1.
*MS analysis results (raw data) for calibration samples, Table 2.
◊◊Concentrations from linear regression of background-corrected results.

EXAMPLE 3

Example 3 presents mass spectrometric data for calibration standards of various chemical reference materials prepared in high-purity air, analyzed in conjunction with analysis system 10 metered via manifold 20 in real time. Calibration gas standards were prepared as described in Example 1 for various chemical constituents, including, e.g., methyl n-butyl ketone (CAS# 591-78-6), methyl iodide (CAS# 74-88-4), styrene (CAS# 100-42-5), ethyl benzene (CAS# 100-41-4), and Freon-113 (CAS# 76-13-1). Tables 4 and 5 list regression results from intensity-derived, background subtracted mass-spectrometric data for standards analyzed. Data were analyzed using KaleidaGraph (Synergy Software Technologies, Inc., Essex Junction, Vt.). No limitations are intended.

TABLE 4

Regression results from intensity-derived, background subtracted mass-spectrometric data for various chemical reference materials prepared in high-purity air as calibration standards.

| Methyl Iodide | | Ethyl Benzene | | Styrene | |
|---|---|---|---|---|---|
| Intensity | Conc.* (ppb) | Intensity | Conc.* (ppb) | Intensity | Conc.* (ppb) |
| 2.0000 | 2.4600 | 1.0000 | 3.0000 | 28.0 | 55.0 |
| 21.000 | 24.630 | 5.0000 | 25.000 | 103.0 | 243.0 |
| 122.00 | 123.13 | 112.00 | 501.00 | 1155.0 | 2873.0 |
| 913.00 | 985.07 | 225.00 | 1252.0 | 1943.0 | 4842.0 |
| 1346.0 | 1231.3 | 465.00 | 2503.0 | 3953.0 | 9869.0 |
| 2577.0 | 2462.7 | 862.00 | 5006.0 | 8437.0 | 21080 |
| 4492.0 | 4925.4 | — | — | 10864 | 27147 |
| — | — | — | — | 27781 | 69441 |
| — | — | — | — | 1.0284E+05 | 2.5710E+05 |
| [b] = | 0.45074 | [b] = | −2.324 | [b] = | −14.049 |
| [m] = | 1.0181 | [m] = | 5.3426 | [m] = | 2.4938 |
| R² = | 1.0 | R² = | 1.000 | R² = | 1.000 |

*Conc. = m[x] + b, where x = Intensity

TABLE 5

Regression results from intensity-derived, background subtracted mass-spectrometric data for various chemical reference materials prepared in high-purity air as calibration standards.

| Methyl n-Butyl Ketone ◊ | | Freon-113 | |
|---|---|---|---|
| Intensity | Conc.* (ppb) | Intensity | Conc.* (ppb) |
| 0.00 | 0.00 | 52.130 | 5.1200 |
| 5.00 | 6.0 | 105.75 | 51.170 |
| 17.8 | 21.0 | 554.44 | 383.77 |
| 89.2 | 106.0 | 1330.6 | 1023.4 |
| 141.0 | 169.0 | 1872.7 | 2046.8 |
| 373.0 | 445.0 | 3164.8 | 2558.5 |
| 538.0 | 642.0 | 6364.9 | 5117.0 |

TABLE 5-continued

Regression results from intensity-derived, background subtracted mass-spectrometric data for various chemical reference materials prepared in high-purity air as calibration standards.

| Methyl n-Butyl Ketone ◊ | | Freon-113 | |
|---|---|---|---|
| Intensity | Conc.* (ppb) | Intensity | Conc.* (ppb) |
| 963 | 1149.0 | 11965 | 10234 |
| 2286.0 | 2728.0 | 1.2157E+05 | 1.0234E+05 |
| 3917.0 | 4675.0 | — | — |
| 76826 | 91684 | — | — |
| [b] = | −3.2E−167 ◊ | [b] = | −40.117 |
| [m] = | 1.1926 | [m] = | 0.8624 |
| $R^2$ = | 1.0 | $R^2$ = | 0.99999 |

*Conc. = m[x] + b, where x = Intensity
◊ Forced origin

EXAMPLE 4

Example 4 details real-time monitoring/analysis of a sampling environment 30 configured as illustrated in FIG. 5a for animal exposure studies via monitoring/analysis of the animal's breath.

Figure 11:
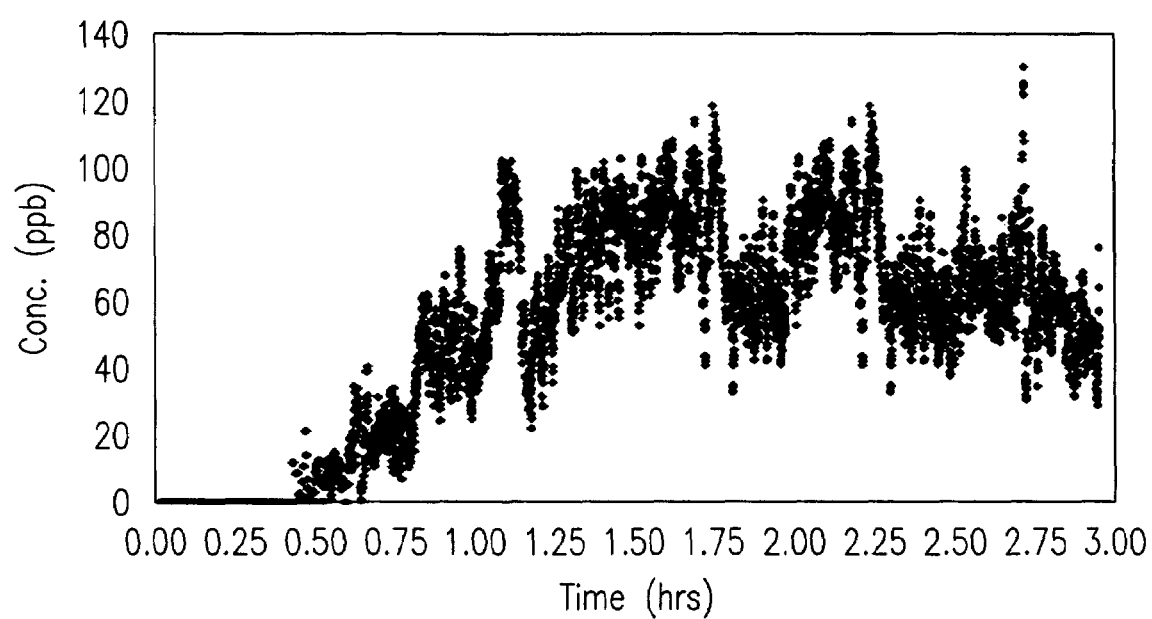
FIG. 11 presents mass-spectrometric data collected in real-time from a sampling environment configured for exposure studies in conjunction with the invention for monitoring and detection of toluene in expired breath of a live rat as a function of time.

A custom made ~3-cc glass cup bulb 34 including a septum (not shown) made of silicon sealant (Dow Corning, Baltimore, Md.) was affixed to the dermis of an anesthetized ~253 g rat 32 using a veterinary bonding compound (e.g., vet bond®, 3M, St. Paul, Minn.) and allowed to affix for ~12 to 14 hours. Approximately 0.0007 g (7.0161 g-7.0154 g by weight) toluene [CAS# 56-81-5] (Sigma-Aldrich, St. Louis, Mo.) was delivered via precision syringe 36 (e.g., a Hamilton lock-tight® syringe, Hamilton USA, Reno, Nev.) to glass bulb 34 and the active animal 32 was placed in a (e.g., a 10-L) glass sampling chamber 30 (sampling environment) filled with high-purity air from source 205 through a flexible 20-L Tedlar® gas sampling bag (Cole-Palmer Instrument Company, Vernon Hills, Ill.) 210 thereby maintaining a constant sample volume and/or flow to manifold 20. Chamber 30 was coupled to manifold 20 and further to bag 210 and source 205 via ¼-inch tubing 5 made of polytetrafluoroethylene (also known as Teflon®, DuPont, Wilmington, Del.), but is not limited thereto. Manifold 20 was further coupled via ¼-inch stainless steel tubing 4 to mass-selective analysis system 10 comprising an on-line quadrupole mass spectrometer (e.g., an Agilent model 5973N quadrupole mass spectrometer, Agilent Technologies, Inc., Santa Clarita, Calif.). System 10 was calibrated using toluene standards prepared in 3-liter sampling bags (e.g., SKC Tedlar®, available commercially from Cole-Palmer Instrument Company, Vernon Hills, Ill. 60061-1844) as described in Example 1 at concentrations in the range from about 2 ppb to about 1500 ppb in high-purity air. Throughput valve 24 of manifold 20 was set to a flow rate matching the published breathing rate for animal 32 (i.e., 199 mL/min). Alternatively, breathing rate can be determined using a breathing plethysmograph (e.g., a double chamber plethysmograph, Buxco Electronics, Inc., Wilmington, N.C.). Flow of high-purity air into (reservoir) bag 210 was set at ~250 mL/min to ensure no backflow contamination of system 10 creating an "on-demand" sampling environment 30. Inlet valve 22 was adjusted to a instrument vacuum pressure in the range from about $0.5 \times 10^{-5}$ Torr to about $5 \times 10^{-6}$ Torr that maximized response to the desired analyte, i.e., toluene (m/z=92). Final throughput rate was 195 mL/min following analyte detection optimization. Sample chamber 30 was monitored in conjunction with analysis system 10 at a sampling rate of 0.8 scans/sec for five (5) consecutive periods of 30 minutes each. Sampling chamber 30 was monitored in real-time in conjunction with manifold 20 via analysis of samples collected from chamber 30 through manifold 20 until toluene (m/z=92) was detected and quantified in the mass-selective instrument of system 10. Data were also collected on the euthanized animal 32 in a post-exposure period of about 30 minutes ensuring no leaking of reference chemical from bulb 34. Mass spectrometer was operated in conjunction with sample analysis software (e.g., MS Sensor® software, Diablo Analytical, Inc., Concord, Calif.) providing quantitative monitoring/analysis of analytes sampled from chamber 30. FIG. 11 illustrates mass-spectrometric results for toluene clearance from rat 32 as a function of time in chamber 30 in real-time. Time from exposure to detection of the toluene analyte from the respired breath of animal 32 in sampling environment 30 was approximately 30 minutes. Each data point represents an average of 10 sampling points collected at 0.8 scans/sec. Data were used to develop Physiologically-Based Pharmacokinetic (PBPK) Models correlating to human exposure, as described by Poet et al. (*Toxicological Sciences* 67,17-31, 2002).

Results show the method and apparatus of the invention permit real-time conformational sampling and monitoring of a sampling environment achieving part-per-billion (ppb) detection limits for target analytes of interest. All flow rates (e.g., of throughput valve 24 in manifold 20) conforming with sampling events of the sampling environment 30 that further conform with the vacuum or operational pressure requirements of mass-selective detectors, components, and/or instruments of analysis system 10 may be employed without limitation.

As will be understood by those of skill in the art, various data correction approaches can be used to correct mass spectrometric data for (i) response variations due to humidity, (ii) vacuum variances, (iii) environmental and/or sampling backgrounds (intensities), (iv) data point multiplicity, (v) subtractive percent determination of daughter products (i.e., determination of the percent intensity contribution from a co-eluting analyte at same analytical mass), and the like. Techniques used for correcting mass spectrometric data include, but are not limited to, e.g., blank subtraction, data point averaging, ratioing (e.g., intensity of analyte to intensity of endogenous species), and the like. No limitations are intended.

While the preferred embodiments of the present invention have been shown and described, it will be apparent to those skilled in the art that many changes and modifications may be made without departing from the invention in its true scope and broader aspects.

I claim:

1. A method, comprising:
   providing a manifold having: a throughput valving means operable for coupling to an atmospheric sampling environment or volume; an inlet valving means for introducing an atmospheric or other sample containing an analyte(s) of interest into a mass-selective detector, component, or instrument; a fractioning means operably coupled to: (i) a pumping means, (ii) said inlet valving means, and (iii) said throughput valving means for fractioning said sample; and,
   wherein said manifold is fully conformational with said sampling environment and said detector, component, or instrument whereby a selectable flow of said sample is introduced from said sampling environment or volume into said manifold by means of said throughput valving means and further into said mass-selective detector, component, or instrument at the operational vacuum or pressure for said detector, component, or instrument by means of said inlet valving means, the coordinated operation of said throughput valving means and said inlet valving means permitting sampling, monitoring, and/or analysis of said analyte(s) in said sampling environment in real-time.

2. The method of claim 1, wherein said sampling environment or volume is an oxygen-rich sampling environment or volume.

3. The method of claim 2, wherein said operational vacuum or pressure is in the range from about $0.5 \times 10^{-5}$ Torr to about $5 \times 10^{-6}$ Torr operable for monitoring and/or analysis of said analyte(s) in said oxygen-rich sampling environment or volume in real time.

4. The method of claim 1, wherein said sampling environment or volume is an oxygen-deficient sampling environment or volume.

5. The method of claim 4, wherein said operational vacuum or pressure is up to about 708 Torr operable for monitoring and/or analysis of said analyte(s) in said oxygen-deficient sampling environment in real time.

6. The method of claim 1, wherein said manifold is incorporated in a system for monitoring/analysis of a headspace(s) or volume.

7. The method of claim 1, wherein said manifold is a component of a real-time offgassing, exhausting, and/or vehicle emission monitoring or detection system.

8. The method of claim 1, wherein said manifold is a component of a system or device for real-time monitoring/detection of toxic, environmentally hazardous chemical and/or biological agents, or industrially generated analytes in a sampling environment or volume.

9. The method of claim 1, wherein said manifold is operably connected to a mass-selective detector or other mass-selective component, or is itself a component of a mass-selective instrument system.

10. A method for sampling, monitoring, and/or analysis of a gaseous atmospheric sampling environment in real time, comprising:
   providing a gas transfer manifold comprising:
      (i) a inlet (valving) means having a selectable flow rate for metering a sample into a mass-selective detector, component, and/or instrument;
      (ii) a throughput (valving) means having a selectable flow rate operably disposed with said sampling environment or volume, whereby said sample is introduced to said manifold from said environment transferring through said manifold to said instrument, component, and/or detector;
      (iii) a sample fractioning means operably disposed between said throughput (valving) means and said inlet (valving) means for fractioning of said sample in conjunction with a pumping means;
      (iv) a pumping means operably disposed with said fractioning means for pulling said sample through said manifold and/or for scrubbing particulates from said sample, whereby a desired vacuum pressure to said detector, component, and/or instrument is maintained, whereby the operation of said gas manifold comprises:
   determining a throughput value for sampling of said sampling environment or volume;
   setting said throughput valving means at said throughput value for sampling of said sampling environment;
   initiating said pumping means filling said manifold with said sample containing an analyte(s) of interest from said sampling environment and transferring said sample(s) to said mass-selective detector, component, and/or instrument;
   setting said inlet valving means at a flow rate wherein the pressure of said sample introduced into said instrument, component, or mass-selective detector substantially adapting to the operational pressure or vacuum of said mass-selective detector, component, and/or instrument; and
   analyzing said analyte of interest in conjunction with said mass-selective detector, component, and/or instrument, whereby said analyte from said sampling environment or volume is monitored and/or analyzed in real-time.

11. The method of claim 10, wherein said mass-selective instrument is selected from the group consisting of MS/MS, tandem MS, $MS^n$, ion-trap MS, quadrupole MS, ToF MS, FT-ICR MS, or combinations thereof.

12. The method of claim 10, wherein said inlet valving means adjusts dynamically to a pressure or vacuum in the range from about $0.5 \times 10^{-5}$ Torr to about $2.5 \times 10^{-5}$ Torr in response to the flow rate of said throughput valving means.

13. The method of claim 10, wherein said throughput valve introduces a gas sample to said manifold at a flow rate in the range from about 1 mL/min. to about 400 mL/min.

14. The method of claim 10, wherein said fractioning means comprises a member selected from the group consisting of 3-port valve, 4-port. valve, n-port valve, "T" connector, or combinations thereof.

15. The method of claim 10, wherein said mass-selective detector, component and/or instrument further comprises a primary ionization source or filament in a mass spectrometer instrument configuration and/or system.

16. The method of claim 15, wherein said primary ionization source is a glow discharge ionization source.

17. The method of claim 10, wherein said pumping means is selected from the group consisting of foreline pump, vacuum pump, turbo pump.

18. The method of claim 10, further comprising a selective elution system or device for concentration, desorption, and temperature dependent release of a multiplicity of analytes for monitoring/detection of a sampling environment.

19. A gas manifold, comprising:
   a throughput valving means operable for coupling to an atmospheric or other sampling environment;
   an inlet valving means for introducing an atmospheric or environmental sample containing an analyte(s) of interest into a mass-selective detector, component, or instrument;
   a pumping means operably coupled to said inlet valving means and said throughput valving means for pulling said sample through said manifold; and,
   wherein the manifold is fully conformational with said sampling environment and said detector, component, or instrument whereby a selectable flow of said sample is introduced into said mass-selective detector, component, or instrument at the operational vacuum or pressure for said detector, component, or instrument by said inlet valving means, the coordinated operation of said throughput valving means and said inlet valving means permitting sampling, monitoring, and/or analysis of said analyte(s) in said sampling environment in real-time.

20. The manifold of claim 19, wherein said mass-selective instrument is selected from the group consisting of MS/MS, tandem MS, MS$^n$, ion-trap MS, quadrupole MS, ToF MS, FT-ICR MS, or combinations thereof.

21. The manifold of claim 19, wherein said pressure is in the range from about $0.5 \times 10^{-5}$ Torr to about $2.5 \times 10^{-5}$ Torr operable for monitoring and/or analysis of said analyte(s) in an oxygen-rich sampling environment in real time.

22. The manifold of claim 19, wherein said inlet valving means comprises a digital mass flow controlled inlet valve whereby said operational vacuum pressure of said mass-selective detector, component, and/or instrument is maintained.

23. The manifold of claim 19, wherein said pressure is up to about 608 torr operable for monitoring and/or analysis of said analyte(s) in an oxygen-deficient sampling environment in real time.

24. The manifold of claim 19, wherein said operational vacuum or pressure is measured in conjunction with an ion gauge vacuum monitor.

25. The manifold of claim 19, wherein said inlet valving and throughput valving means are selected from the group consisting of electric or pneumatic vacuum valves, pressure valves, mass-flow controller, metering valves, digital versions thereof, and combinations thereof.

26. The manifold of claim 19, further comprising a selective elution system or device for capture, desorption, concentration, and temperature dependent release of a multiplicity of analytes collected from a sampling environment permitting monitoring/detection of said analytes from said environment in real-time.

27. The manifold of claim 19, wherein said manifold is a component of a system for monitoring/analysis of a sampling environment comprising a head-space(s) or volume in real-time.

28. The manifold of claim 19, wherein said manifold is a component of a real-time offgassing, exhausting, and/or vehicle emission monitoring or detection system.

29. The manifold of claim 19, wherein said manifold is a component of a system or device for real-time monitoring/detection of toxic, environmentally hazardous chemical and/or biological agents, or industrially generated analytes in a sampling environment or volume.

30. The manifold of claim 19, wherein said manifold is a component of a mass-selective detector, mass-selective component, or mass-selective instrument system.

31. A gas manifold, comprising:
adjustable throughput valving means operable for coupling to an atmospheric sampling environment;
adjustable inlet valving means for, introducing a gas sample into a mass-selective detector, component, or instrument;
fractioning means operably coupled to: (i) a pumping means, (ii) said inlet valving means, and (iii) said throughput valving means; and,
wherein said throughput valving means and said inlet valving means are operably coupled providing coordinated adjustment whereby said manifold is fully conformational with both said sampling environment and said detector, component, or instrument, said manifold introducing a selectable flow of said gas sample into said mass-selective detector, component, or instrument at a operational vacuum or pressure optimized for said detector, component, and/or instrument operable for sampling, monitoring, and/or analysis of an analyte(s) from said atmospheric sampling environment in real-time.

32. The manifold of claim 31, wherein said fractioning means comprises a vacuum pump and a member selected from the group consisting of vacuum T-union, 3-way union, 4-way union, 3-way connector, T-connector, 4-way connector, or combinations thereof.

33. The manifold of claim 31 wherein said fractioning means comprises a foreline vacuum pump, said fractioning means operably linked with said inlet valve for fractionating the amount of said gas sample input to said mass-selective detector, selective detector, component, and/or instrument thereby maintaining said operational vacuum or pressure of said mass-selective detector, component, and/or instrument.

34. The manifold of claim 31, further comprising a particulate trap disposed between said pumping means and said fractioning means for trapping particulates removed from said sample permitting characterization of said particulates.

35. The manifold of claim 31, wherein said manifold is a component of a particulate analysis instrument or system.

* * * * *

UNITED STATES PATENT AND TRADEMARK OFFICE
CERTIFICATE OF CORRECTION

PATENT NO. : 7,288,760 B2  Page 1 of 1
APPLICATION NO. : 11/165082
DATED : October 30, 2007
INVENTOR(S) : Karl K. Weitz It is certified that error appears in the above-identified patent and that said Letters Patent is hereby corrected as shown below:

On the cover page under (57) Abstract, "sepectrometric" should read --spectrometric--.

Column 4, line 40, remove the hyphen between to-the.

Signed and Sealed this

Twenty-fifth Day of November, 2008

JON W. DUDAS
*Director of the United States Patent and Trademark Office*